United States Patent [19]

Yamamoto et al.

[11] Patent Number: 5,061,067
[45] Date of Patent: Oct. 29, 1991

[54] ELECTROPHORESIS PATTERN ANALYZER FOR GENETIC MATERIAL

[75] Inventors: Takekazu Yamamoto; Masakazu Nakagawa; Masayoshi Momiyama, all of Tokyo, Japan

[73] Assignee: Aisin Seiki Kabushiki Kaisha, Kariya, Japan

[21] Appl. No.: 330,289

[22] Filed: Mar. 29, 1989

[30] Foreign Application Priority Data

Mar. 31, 1988 [JP] Japan .................................. 63-79500

[51] Int. Cl.$^5$ .................... G01N 21/00; B01D 61/42; C25D 13/00
[52] U.S. Cl. ............................... 356/344; 204/299 R; 204/182.8
[58] Field of Search ..................... 356/344; 204/182.8, 204/299 R

[56] References Cited

U.S. PATENT DOCUMENTS

| | | | |
|---|---|---|---|
| 3,783,117 | 1/1974 | Bean | 356/344 |
| 4,429,996 | 2/1984 | Kamachi | 356/344 |
| 4,832,815 | 5/1989 | Kambara | 204/182.8 |

Primary Examiner—John F. Niebling
Assistant Examiner—Caroline Koestner
Attorney, Agent, or Firm—Burns, Doane, Swecker & Mathis

[57] ABSTRACT

An electrophoresis pattern analyzer for genetic material of this invention comprises: an image data generating means for optically reading an electrophoresis specimen and outputting datum image data corresponding to a datum region and sample image data corresponding to at least one sample region; a datum band pattern retrieving means for retrieving datum band patterns concerning position coordinates of the bands of the datum region in the direction of electrophoresis and two-dimensional forms of the bands of the datum region from the datum image data; a sample band pattern retrieving means for retrieving sample band patterns concerning position coordinates of the bands of the sample region in the direction of electrophoresis and two-dimensional forms of the bands of the sample region from the sample image data; and a band pattern comparing means for comparing the datum band patterns with the sample band patterns and determining characteristics of the sample region. The electrophoresis pattern analyzer for genetic material of this invention provides advantages of more precise, less expensive and higher speed analysis and identification than the conventional visual analysis and identification.

8 Claims, 5 Drawing Sheets

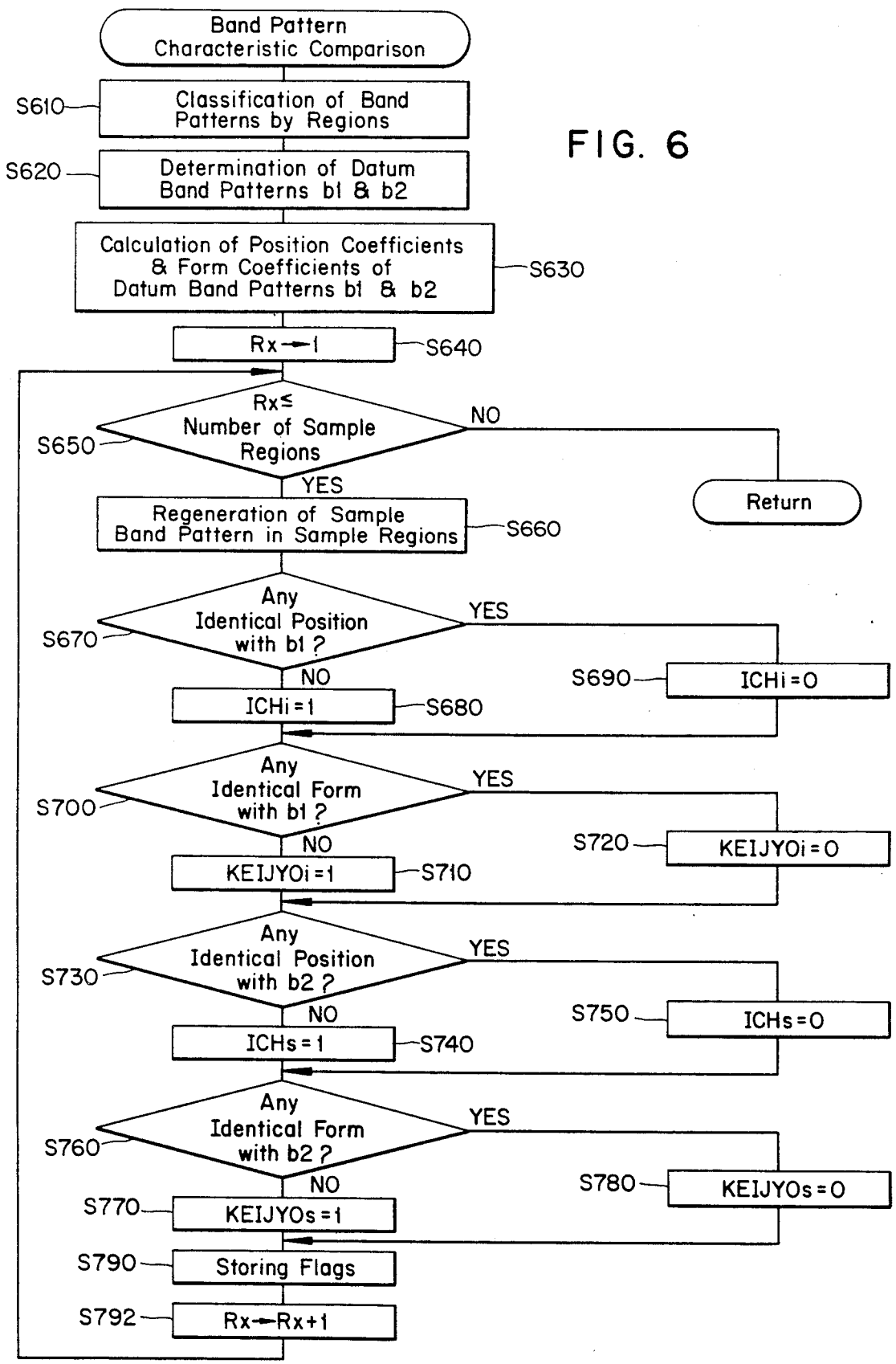

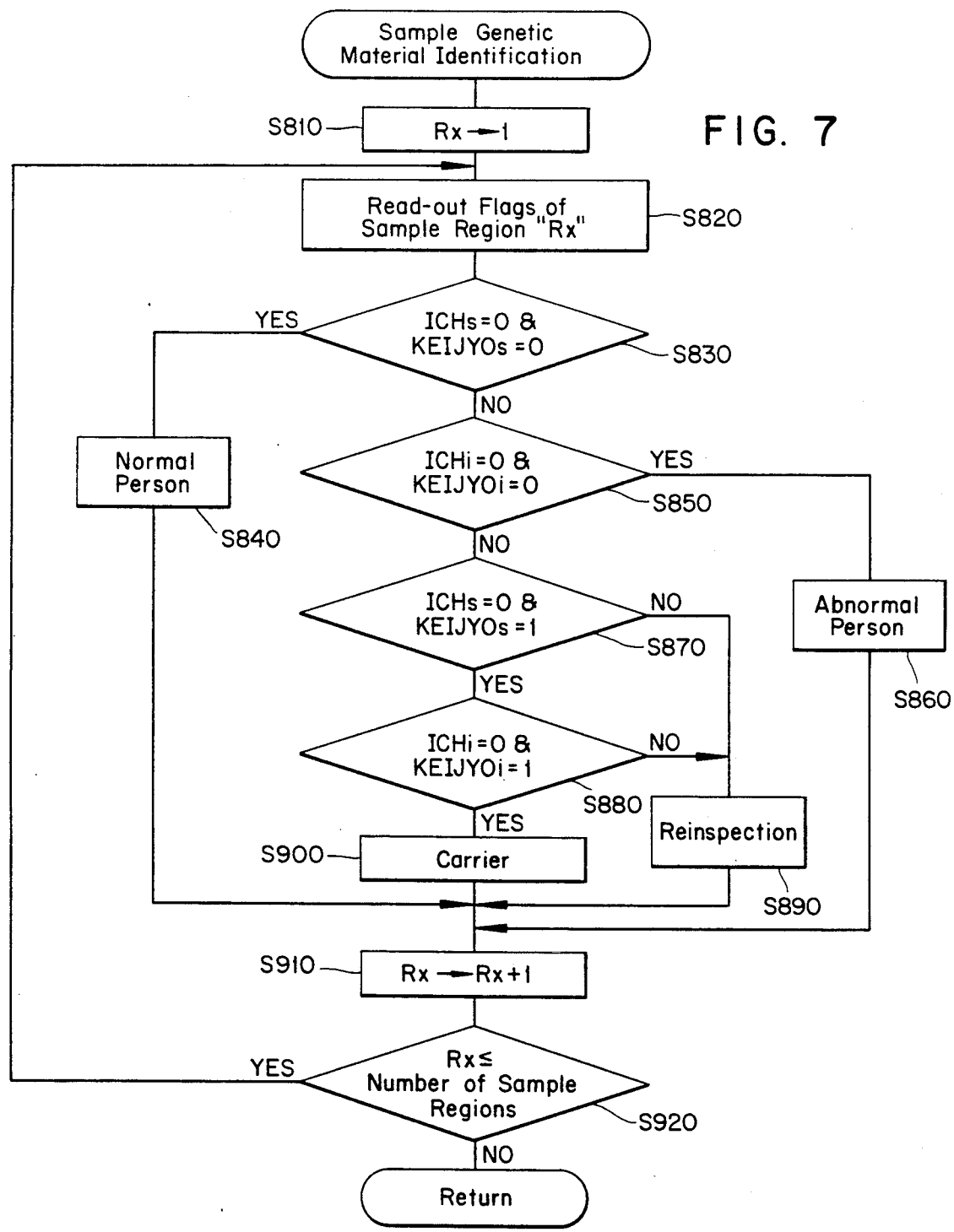

ELECTROPHORESIS PATTERN ANALYZER FOR GENETIC MATERIAL

BACKGROUND OF THE INVENTION

1. Field of the Invention

This invention relates to an electrophoresis pattern analyzer for genetic material suitable for detection and identification of a gene, such as DNA, RNA and a material generated by the gene. The analyzer of this invention is applicable to disease diagnosis, parent-children judgment, physical constitution diagnosis, and cattle and plant breeding judgment.

2. Description of the Prior Art

The southern plotting method, the northern plotting method and the western plotting method have been known for analyzing electrophoresis patterns of a genetic material, such as DNA, RNA and proteins generated by genes (hereinafter referred to as generated proteins). These methods have been employed to detect and identify genes and generated proteins.

In all of these methods, a datum genetic material and a sample genetic material are disposed perpendicularly to the direction of electrophoresis, and are simultaneously effected to migrate electrically for a predetermined period of time. The result of the electrophoresis of the datum and sample genetic material is visually identified.

For instance, an electrophoresis specimen 100, as shown in FIG. 3, results from the southern plotting method. The electrophoresis specimen 100 comprises a datum region 101 defined by the electrophoresis region of the datum genetic material, and sample regions 102, 103 and 104 defined by the electrophoresis regions of the respective sample genetic materials. The datum region 101 has large and intense bands B1 and B2 at 1.35 kb and 1.15 kb of a coordinate axis in the direction of electrophoresis. The sample region 102 has a large and intense band B3 at 1.35 kb of the coordinate axis in the direction of electrophoresis. The sample region 103 has a large and intense band B4 at 1.15 kb of the coordinate axis in the direction of electrophoresis. The sample region 104 has small and slightly intense bands at 1.35 kb and 1.15 kb of the coordinate axis in the direction of electrophoresis. Here, kb, the unit of the coordinate axis in the direction of electrophoresis means a segment length of DNA.

An observer has detected and identified sample genetic materials by visually comparing the bands B3, B4, B5 and B6 of the sample regions 102, 103 and 104 with the bands B1 and B2 of the datum region.

In the above-mentioned current methods, the electrophoresis specimen should be visually observed to identify whether electrophoresis distances of the bands B3, B4, B5 and B6 of the sample regions 102, 103 and 104 agree with the bands B1 and B2 of the datum region 101.

However, the identification was hard to do in the following cases:

(1) Two bands are neighboring too close in the electrophoresis direction.

(2) There are many number of bands in the datum region or the sample regions.

(3) There are many number of genetic materials arranged in one (1) electrophoresis sample. If this is the case, the bands of the sample regions away from the datum region are hard to identify.

(4) There is less amount of the datum genetic material or the sample genetic material. If this is the case, the bands formed are too small and light to identify.

(5) There is large amount of the datum genetic material or the sample genetic material. If this is the case, the bands formed are too large to compare the electrophoresis distances, and two neighboring bands might overlap each other.

Despite these hardships, the identification of genetic materials must be done precisely. Accordingly, it takes rather long time to identify them.

Further intervals between two neighboring bands should be set longer to make the identification easier. Accordingly, the electrophoresis time becomes longer. Because the electrophoresis specimen should be made larger to set the electrophoresis time longer for easier identification, the identification time becomes longer and the identification cost increases.

SUMMARY OF THE INVENTION

It is therefore an object of this invention to provide an electrophoresis pattern analyzer for genetic material enabling to analyze an electrophoresis specimen having a plurality of sample genetic materials precisely in a short period of time, thereby overcoming the above-mentioned hardships.

An electrophoresis pattern analyzer for genetic material comprises:

an image data generating means for optically reading an electrophoresis specimen having a datum region with a plurality of bands arranged in a direction of electrophoresis and at least one sample region with a plurality of bands arranged in said direction of electrophoresis and said bands which are obtained by simultaneously migrating at least one datum genetic material disposed perpendicularly to said direction of electrophoresis and at least one sample genetic material disposed perpendicularly to said direction of electrophoresis electrically, and outputting datum image data corresponding to said datum region and sample image data corresponding to said sample region;

a datum band pattern retrieving means for retrieving datum band pattern concerning position coordinates of said bands of said datum region in said direction of electrophoresis and two-dimensional forms of said bands of said datum region from said datum image data;

a sample band pattern retrieving means for retrieving sample band patterns concerning position coordinates of said bands of said sample region in said direction of electrophoresis and two-dimensional forms of said bands of said sample region from said sample image data; and a band pattern comparing means for comparing said datum band patterns with said sample band patterns and determining characteristics of said sample region.

Genetic materials including genes, such as DNA, RNA and proteins generated by the genes, are analyzable with the electrophoresis pattern analyzer for genetic material of this invention. These genetic materials are generally charged negatively, and can migrate electrically in fluid with an electric field applied. The datum genetic material is a genetic material whose species has been already known. The sample genetic material is a genetic material whose species should be determined.

The electrophoresis specimen is obtained by simultaneously migrating the datum genetic material and a plurality of the sample genetic materials electrically.

Specifically speaking, the electrophoresis specimen is obtained by the following manner:

The datum genetic material and a plurality of the sample genetic materials are disposed perpendicularly to the direction of electrophoresis in an electrophoresis allowing member like an agar gel. The datum genetic material and a plurality of the sample genetic materials ar electrically migrated simultaneously in the electrophoresis direction, and the electrophoresis is terminated simultaneously. Thus, the electrophoresis specimen is obtained.

In order to perform the image identification processing later described, it is preferred to mark the genetic materials during or after the electrophoresis. For the marking, the following are available: coloring with dyes, coloring with fluorescent materials, and radiation with radioactive isotopes. It is also preferred to incorporate these dyes, fluorescent materials and radioactive isotopes into the genetic materials after the electrophoresis. The electrophoresis specimen may comprise an agar gel in which the datum genetic material and a plurality of the sample genetic material are disposed, and the agar gel which extends in both the electrophoresis direction and the genetic materials disposition direction. In addition, the electrophoresis specimen may be a film of various kinds for photographing the agar gel after the electrophoresis.

The datum region means a region in the electrophoresis specimen where the datum genetic material is allowed to electrically migrate, or a recording region in the electrophoresis specimen. One (1) datum region may be provided for an electrophoresis specimen, or a plurality of datum regions may be provided for an electrophoresis specimen. Further, a plurality of the datum regions having bands different from each other may be provided for an electrophoresis specimen.

The sample region means a region in the electrophoresis specimen where the sample genetic materials are allowed to electrically migrate, or a recording region in the electrophoresis specimen. One (1) or more of the sample regions are provided for an electrophoresis specimen.

The bands are regions in the datum region and the sample region where genetic materials of an identical molecular weight are accumulated. The genetic materials of an identical molecular weight migrate electrically in a substantially identical distance, and they accumulate in a band shape at a specific position in the datum region and the sample regions.

The image data generating means reads the electrophoresis specimen optically, and converts the results of the reading into image data as electric signals. The image data generating means also outputs the datum image data as the image data of the datum region and the sample image data as the image data of the sample regions. The image data generating means may comprise a linear image sensor, an area image sensor, a laser scanning means and a photo detecting means thereof, or a ultraviolet generating means for generating fluorescence and a photo multiplier as a photo detecting means thereof.

The datum band pattern retrieving means is an image processing means for retrieving the datum band patterns from the obtained datum image data. The datum band patterns are pattern information of the bands of the datum region. The datum band pattern retrieving means may comprise an image processor incorporating a micro processor of an exclusive application or a general application. The datum band patterns may be image information comprising centroids positions of the bands of the datum region in the electrophoresis direction and forms of the bands of the datum region.

The sample band pattern retrieving means is an image processing means for retrieving the sample band patterns from the obtained sample image data. The sample band patterns are pattern information of the bands of the sample regions. The sample band pattern retrieving means may comprise an image processor incorporating a micro processor. The sample band patterns may be image information comprising centroids positions of the bands of the sample regions in the electrophoresis direction and forms of the bands of the sample regions.

The band pattern comparing means is an image processing means for comparing the obtained datum band patterns with the sample band pattern and determining species of the sample regions. The band pattern comparing means may comprise an image processor incorporating a micro processor. The band pattern comparing means determines whether the sample genetic materials are identical with a part of the datum genetic material or all of the datum genetic material, or whether they are different from a part of the datum genetic material or all of the datum genetic material.

For instance, HIDIC-IP/200 manufactured by Hitachi Ltd. may be employed for the above-mentioned image processor.

In the electrophoresis pattern analyzer for genetic material of this invention, the image data generating means reads the electrophoresis specimen optically, and outputs the datum image data as the image data of the datum region and the sample image data as the image data of the sample regions. The datum band pattern retrieving means retrieves the datum band patterns concerning the bands of the datum region from the obtained datum image data. The sample band pattern retrieving means retrieves the sample band patterns concerning the bands of the sample regions from the obtained sample image data. The band pattern comparing means compares the datum band patterns with the sample band patterns and determines species of the sample regions. For instance, the band pattern comparing means determines whether the sample genetic materials are identical with a part of the datum genetic material or all of the datum genetic material, or whether they are different from a part of the datum genetic material or all of the datum genetic material.

Thus, the electrophoresis pattern analyzer for genetic material of this invention enables to precisely detect and identify the sample genetic materials even when there are increased number of the sample genetic materials and even when neighboring bands are close to each other, since the electrophoresis pattern analyzer for genetic material of this invention performs the image processing of the electrophoresis specimen, obtained by simultaneously migrating at least one of the datum genetic material and one or more of the sample genetic materials electrically, in the manner described above.

As described above, the electrophoresis pattern analyzer for genetic material of this invention comprises the image data generating means for photographing the electrophoresis specimen having the datum band region and at least one of the sample region, the band pattern retrieving means for processing output signals from the image data generating means, the sample band pattern retrieving means and the band pattern comparing means. Accordingly, independent of number of specimens, the electrophoresis pattern analyzer for genetic material of this invention can analyze the electrophoresis specimen more precisely than the conventional visual analysis and identification.

Further, the electrophoresis pattern analyzer for genetic material of this invention enables precise analyzing and identifying even when there are less amount of datum and sample genetic materials in the electrophoresis specimen, even when the electrophoresis time is shortened and even when there are an increased number of sample regions as many as 100 or more in the electrophoresis specimen.

Thus, the electrophoresis pattern analyzer for genetic material of this invention provides advantages of less expensive and higher speed analyzing and identifying compared with the conventional visual analyzing and identifying.

BRIEF DESCRIPTION OF THE DRAWINGS

A more complete appreciation of this invention and many of the attendant advantages thereof will be readily obtained as the same becomes better understood by reference to the following detailed description when considered in connection with the accompanying drawings, wherein:

FIG. 6 is a flowchart of another subroutine program for the main routine program of the preferred embodiment of the electrophoresis analyzer for genetic material according to this invention; and FIG. 7 is a flowchart of a still another subroutine program for the main routine program of the preferred embodiment of the electrophoresis analyzer for genetic material according to this invention;

DESCRIPTION OF THE PREFERRED EMBODIMENT OF THE INVENTION

Having generally described this invention, a further understanding can be obtained by reference to certain specific preferred embodiments which are provided herein for purposes of illustration only and are not intended to be limiting unless otherwise specified.

Figure 1:
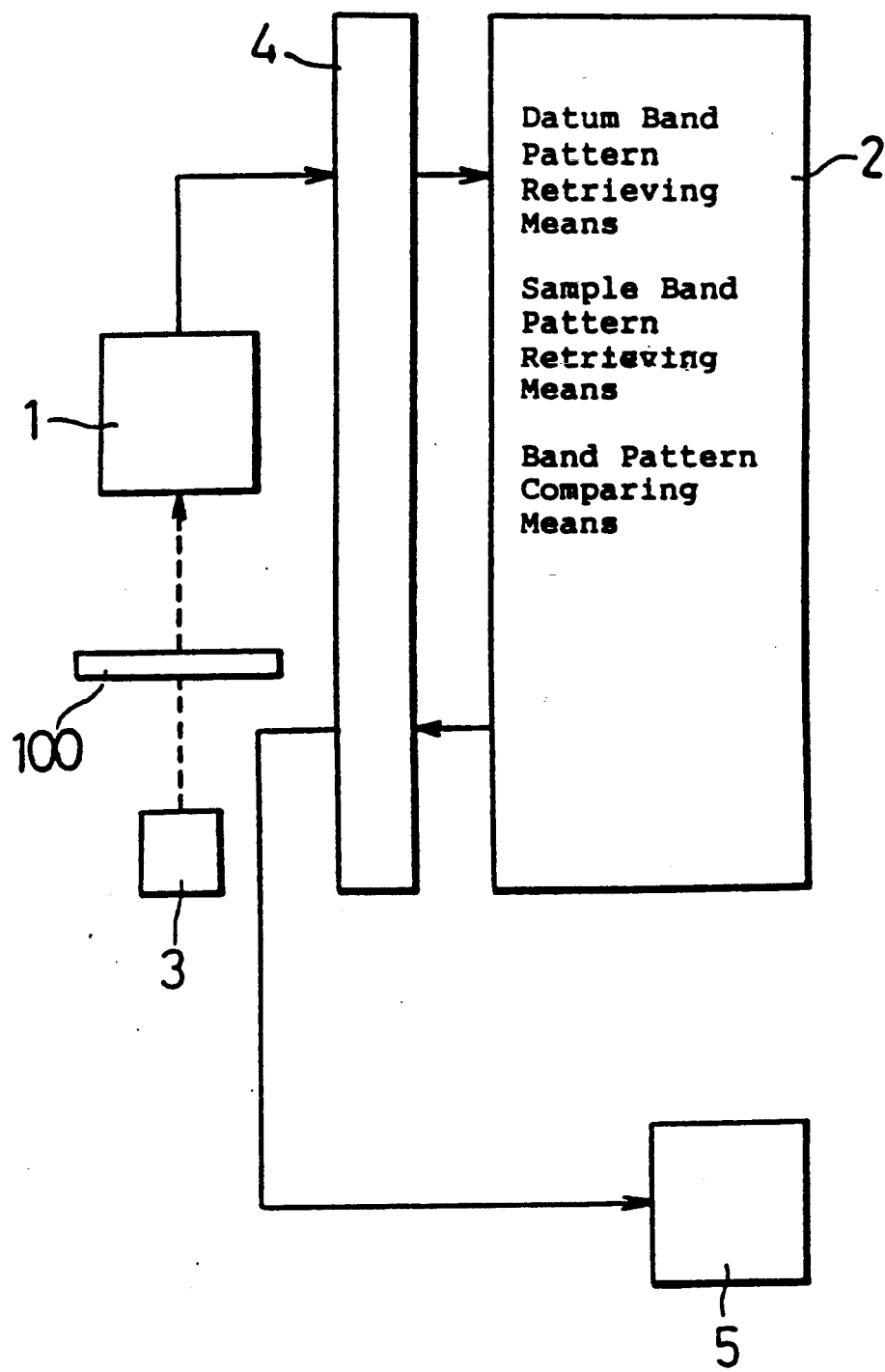
FIG. 1 is a block diagram of a preferred embodiment of an electrophoresis analyzer for genetic material according to this invention.
Figure 2:
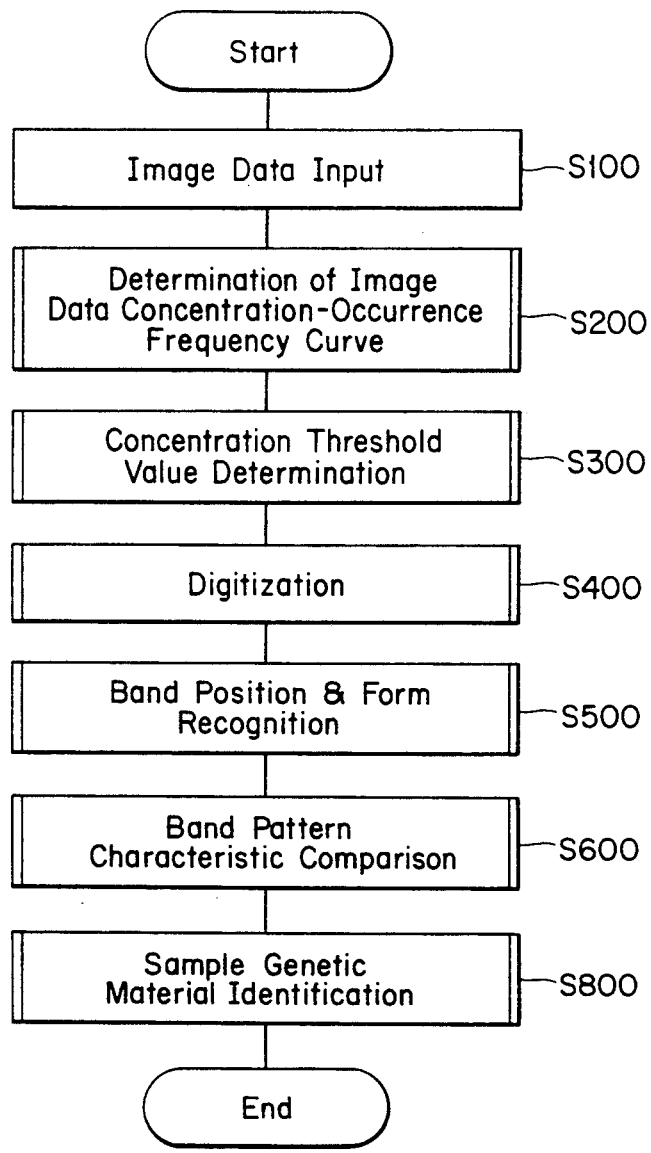
FIG. 2 is a flowchart of a main routine program of the preferred embodiment of the electrophoresis analyzer for genetic material according to this invention.
Figure 3:
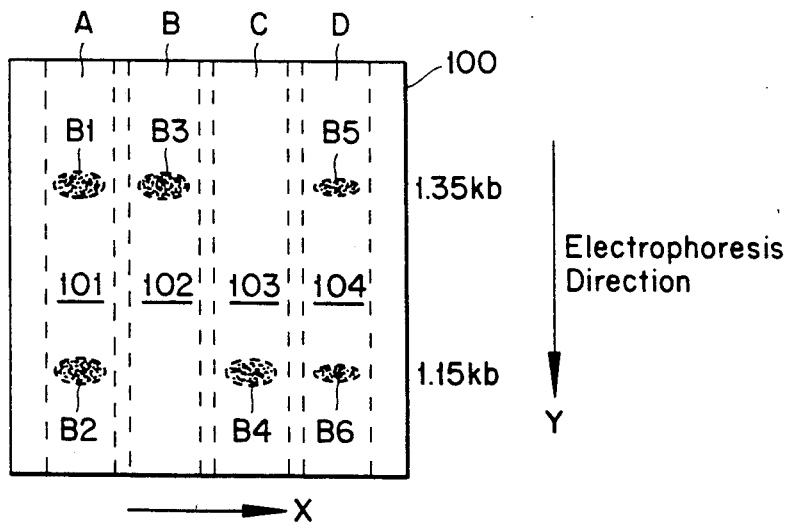
FIG. 3 is a schematic view of a electrophoresis specimen analyzed with the preferred embodiment of the electrophoresis analyzer for genetic material according to this invention.
Figure 4:
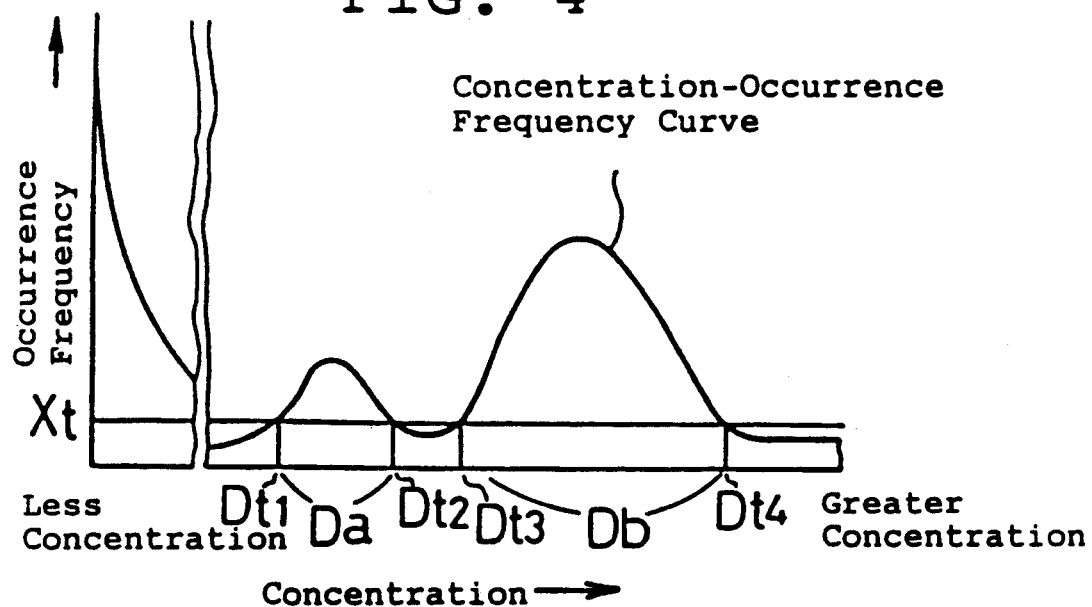
FIG. 4 is a histogram specifying a concentration-occurrence frequency relationship in the electrophoresis specimen.
Figure 5:
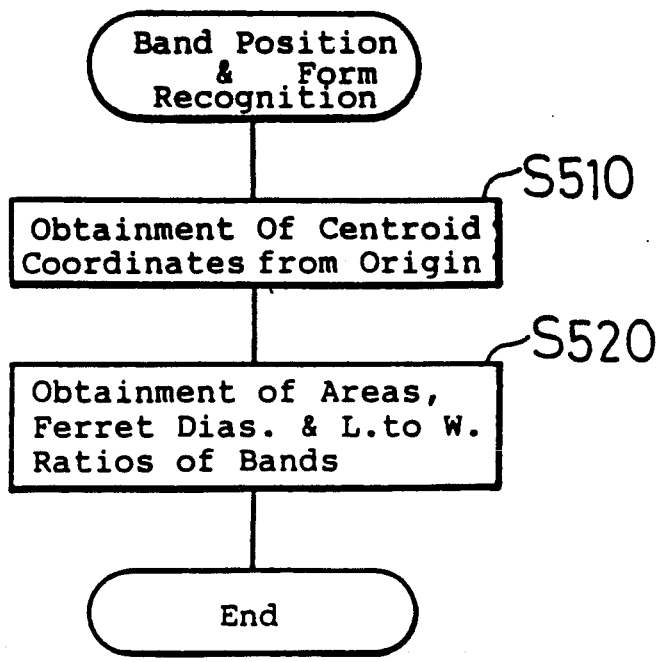
FIG. 5 is a flowchart of a subroutine program for the main routine program of the preferred embodiment of the electrophoresis analyzer for genetic material according to this invention.

A preferred embodiment of an electrophoresis pattern analyzer for genetic material according to this invention will be hereinafter described with reference to the drawings. FIG. 1 is a block diagram of the preferred embodiment of the electrophoresis analyzer for genetic material. FIG. 2 is a flow chart of a main routine program of the preferred embodiment thereof. FIG. 3 is a schematic view of an electrophoresis specimen analyzed with the preferred embodiment thereof. FIG. 4 is a histogram specifying a concentration-occurrence frequency relationship in the electrophoresis specimen. FIGS. 5, 6 and 7 are flow charts of subroutine programs for the main routine program, described in FIG. 2 of the preferred embodiment thereof.

First, the electrophoresis specimen 100 analyzed with the preferred embodiment thereof will be described with reference to FIG. 3. The electrophoresis specimen 100 is identical with the electrophoresis specimen described in the "Description of the Prior Art" section.

This electrophoresis specimen 100 is obtained by verifying DNA suffering from the sickle-cell amemia, one of human hereditary diseases, by the southern plotting method. The electrophoresis specimen 100 has a datum region 101 and sample regions 102, 103 and 104, and is an agar gel of approximately 10 cm $\times$ 10 cm in size. The datum region 101 and the sample regions 102, 103 and 104 are arranged perpendicularly to the direction of the electrophoresis. The datum region 101 is a region where a datum genetic material A later described is allowed to electrically migrate, and the sample regions 102, 103 and 104 are regions where sample genetic materials B, C and D later described are allowed to electrically migrate.

Here, the datum genetic material A is a part of a mixture of DNA of a normal person and DNA of a patient suffering from the sickle-cell amemia. The mixture was obtained by mixing the DNAs and cutting them with a constraint enzyme MstII thereafter. Similarly, the sample genetic material B is a part of DNA of a subject b cut with the constraint enzyme MstII, the sample genetic material C is a part of DNA of a subject c cut with the constraint enzyme MstII, the sample genetic material D is a part of DNA of a subject d cut with the constraint enzyme MstII.

Each of the datum region 101 and the sample regions 102, 103 and 104 respectively includes the datum genetic material A and the sample genetic materials B, C and D. The datum genetic material A and the sample genetic materials B, C and D are arranged for a perpendicular manner to the electrophoresis direction at a predetermined electrophoresis starting position (not shown). Then, they are migrated electrically for a predetermined period of time. After the electrophoresis, they are processed by the southern plotting method to modify them in linear chains and hybridized with a certain DNA probe. Particulars on the processing methods for the genetic materials above-mentioned will not be explained herein.

After the electrophoresis processing, the datum region 101 comes to have a band B1 of the electrophoresis pattern of DNA of a normal person and a band B2 of the electrophoresis pattern of DNA of a patient suffering from the sickle-cell amemia. Similarly, after the electrophoresis processing, the sample regions 102, 103 and 104 come to have bands B3, B4, B5 and B6.

In this electrophoresis specimen 100, the bands B1 and B3 are formed largely and intensely around 1.35 kb of a coordinate axis in the direction of the electrophoresis, the bands B2 and B4 are formed largely and intensely around 1.15 kb of the coordinate axis in the direction of the electrophoresis, and the bands B5 and B6 are formed small and less intensely around 1.35 kb and 1.15 kb of the coordinate axis in the direction of the electrophoresis, respectively.

Now, an arrangement of the preferred embodiment of the electrophoresis pattern analyzer for genetic material according to this invention will be hereinafter described.

As illustrated in FIG. 1, the electrophoresis pattern analyzer for genetic material has a CCD two-dimensional photographing apparatus 1 for photographing the electrophoresis specimen 100 as the image data generating means and an image processing apparatus 2 for processing the image data output by the CCD two-dimensional photographing apparatus 1. Further, the electrophoresis pattern analyzer for genetic material has a back-light type light generating apparatus 3 for lighting the electrophoresis specimen 100 at the rear thereof, an I/O interface 4 and an output display apparatus 5.

The CCD two-dimensional photographing apparatus 1 comprises a built-in CCD area image sensor having 512×512 picture elements. The CCD area image sensor is disposed in parallel to the electrophoresis direction of the electrophoresis specimen 100.

The image processing apparatus 2 has, as illustrated in FIG. 1, a processing unit (not shown) comprising the datum band pattern retrieving means, the sample band pattern retrieving means and the band pattern comparing means, a memory unit (not shown) for storing various image data and a control unit (not shown) for controlling the processing unit, the memory unit and the I/O interface 4.

The light generating apparatus 3 is a xenon lamp, and flashes in a manner synchronizing with the photographing cycle of the CCD two-dimensional photographing apparatus 1.

The output display apparatus 5 is a CRT display.

Next, the operation of the electrophoresis pattern analyzer for genetic material will be hereinafter described. The electrophoresis direction is referred to as the Y-direction, and the perpendicular direction thereof is referred to a the X-direction in order to simplify the description.

The CCD two-dimensional photographing apparatus 1 photographs the electrophoresis specimen 100. Then, the CCD two-dimensional photographing apparatus 1 outputs the image data for each of the picture elements, which is output by the CCD area image sensor (not shown), to the image processing apparatus 2 through the I/O interface 4.

The operation of the image processing apparatus 2 which has received the image data will be hereinafter described with reference to the flowchart of FIG. 2.

The image processing apparatus 2 receives output signals as the image data of the electrophoresis specimen 100 from the CCD two-dimensional photographing apparatus 1 at a step, S100. The received image data includes the datum image data as the image data of the datum region 101 and the sample image data as the image data of the sample regions 102, 103 and 104.

The datum image data and the sample image data are processed altogether to determine a concentration-occurrence frequency curve of the image data at a step, S200. FIG. 4 illustrates the concentration-occurrence frequency curve. The concentration-occurrence frequency curve is obtained by the following manner:

The input image data was divided into picture elements of 512×512 pieces. The output signal of each picture element is taken as one (1) occurrence frequency, and the output signal of each picture element is taken as the concentration to prepare the concentration-occurrence frequency curve.

The concentration-occurrence frequency curve thus obtained is processed to determine concentration threshold values at a step, S300. The determination of the threshold values will be hereinafter described with reference to FIG. 4. The threshold concentration values Dt1, Dt2, Dt3 and Dt4 are obtained from a predetermined occurrence frequency threshold value Xt and the concentration-occurrence frequency curve. Here, the image data, or output signal, corresponding to a concentration range Da, i.e. Dt1 to Dt2, is obtained from the picture elements corresponding to the bands B5 and B6 of the electrophoresis specimen 100. The image data, or output signal, corresponding to a concentration range Db, i.e. Dt3 to Dt4, is obtained from the picture elements corresponding to the bands B1 through B4 of the electrophoresis specimen 100. It is natural that the concentration range Da and the concentration range Db may be continuous when the occurrence frequency threshold value Xt is small.

The image data from all the picture elements is digitized by using thus obtained concentration threshold values, Dt1, Dt2, Dt3 and Dt4 at a step, S400. Here, the picture elements having the image data falling in the concentration ranges Da and Db are taken as a concentration value of on (1) and the picture elements having the image data falling outside the concentration ranges Da and Db are taken as a concentration value of zero (0). Further, all of the image data of the picture elements having concentrations of the minimum concentration threshold value Dt1 or less, which corresponds to regions having less DNA segments, are taken as a concentration value of zero (0).

The digitized image data are processed to recognize two-dimensional centroid coordinates of digitized band patterns and forms thereof at a step, S500. Then, the band patterns b1 through b6 are classified into the datum band patterns b1 and b2 an the sample band patterns b3 through b6 by the centroid coordinates in the X-direction.

The characteristics of the datum ban patterns b1 and b2 are compared with those of the sample band patterns b3 through b6 of the sample region 102, 103 and 104 at a step, S600.

Finally, the identification of the sample genetic materials are performed according to the comparison results at a step, S800.

The band pattern recognizing subroutine program performed in the step, S500, will be hereinafter described with reference to FIG. 5.

The centroid coordinates of the bands B1 through B6 in the X-direction and Y-direction are first calculated at a step, S510. Then, areas, products of ferret diameters and ratios of length to width of the band patterns b1 through b6 are calculated at a step, S520.

The band pattern characteristic comparing subroutine program performed in the step, S600, will be hereinafter described with reference to FIG. 6.

The band patterns b1 through b6 are classified into the datum region 101 and the sample regions 102, 103 and 104 by the centroid coordinates in the X-direction at a step, S610.

The datum band patterns b1 and b2 classified into the datum band region 101 are determined by the centroid coordinates in the Y-direction whether they are normal or abnormal at a step, S620. In this preferred embodiment, the datum band pattern b1 migrating electrically in a shorter distance is abnormal, and the datum band pattern b2 migrating electrically in a longer distance is normal.

Position coefficients, YsnMIN and YsnMAX, and form coefficients, SsnMIN, SsnMAX, FsnMIN, FsnMAX, HsnMIN and HsnMAX, of the datum band patterns b1 and b2 are calculated at a step, S630. The way how to calculate the position coefficients and form coefficients will be later described.

An accumulator Rx built-in in the image data processing apparatus 2 for specifying sample region numbers is increased by 1 at a step, S640. Then, the number set in the accumulator Rx is checked whether it exceeds the number of the sample regions at a step, S650. Here, the number of the sample regions is three (3) in this preferred embodiment. When the set number exceeds the number of the sample regions, this subroutine program is terminated to return the operation to the main routine program. When the set number does not exceed the number of the sample regions, the sample band pattern data in the sample region corresponding to the number set in the accumulator Rx is regenerated at a step, S660.

Here, the number set in the accumulator Rx is one (1) at this stage. Accordingly, the data of the sample band pattern b3 in the sample region 102 is read out. When the number set in the accumulator Rx is two (2), the data of the sample band pattern b4 in the sample region 103 is read out. When the number set in the accumulator Rx is three (3), the data of the sample band patterns b5 and b6 in the sample region 104 is read out.

The position coefficients of the abnormal datum band pattern b1 calculated at S630 are compared with the centroid coordinates of the sample band patter b3 in the sample region 102 to determine whether the sample region 102 has a sample band pattern considered as being at an identical position with the abnormal datum band pattern b1 at a step, S670. When the sample region 102 has such a band pattern, an ICHi flag is set to zero (0) at a step, S690. When the sample region 102 does not have such a band pattern, the ICHi flag is set to one (1) at a step, S680.

The form coefficients of the abnormal datum band pattern b1 calculated at S630 are compared with the form data of the sample band pattern b3 in the sample region 102 to determine whether the sample region 102 has a sample band pattern considered as being an identical form with the abnormal datum band pattern b1 at a step, S700. When the sample region 102 has such a band pattern, a KEIJYOi flag is set to zero (0) at a step, S720. When the sample region 102 does not have such a band pattern, the KEIJOi flag is set to one (1) at a step, S710.

In a method similar to S670, the position coefficients of the normal datum band pattern b2 calculated at S630 are compared with the centroid coordinates of the sample band pattern b3 in the sample region 102 to determine whether the sample region 102 has a sample band pattern considered as being at an identical position with the normal datum band pattern b2 at a step, S730. When the sample region 102 has such a band pattern, an ICHs flag is set to zero (0) at a step, S750. When the sample region 102 does not have such a band pattern, the ICHs flag is set to one (1) at a step, S740.

In a method similar to S700, the form coefficients of the normal datum band pattern b2 calculated at S630 are compared with the form data of the sample band pattern b3 in the sample region 102 to determine whether the sample region 102 has a sample band pattern considered as being an identical form with the normal datum band pattern b2 at a step, S760. When the sample region 102 has such a band pattern, a KEIJYOs flag is set to zero (0) at a step, S780. When the sample region 102 does not have such a band pattern, the KEIJYOs flag is set to one (1) at a step, S770.

Finally, the flags are stored in the memory unit at a step, S790, and one (1) is added to the accumulator Rx at a step, S792.

The above-mentioned operation is performed repeatedly for all the other sample regions 103 and 104 to obtain the above-mentioned flags for all of the sample regions 102, 103 and 104.

The way how to calculate the above-mentioned position coefficients and form coefficients of the datum band pattern b1 and b2 will be hereinafter described.

The position coefficients are the minimum values and the maximum values of the datum band patterns b1 and b2 in the Y-direction, namely YsnMIN and YsnMAX of the Y-coordinate axis. The position coefficients are calculated by the following formulas:

$YsnMIN = Ysn - \alpha Fysn$
$YsnMAX = Ysn + \alpha Fysn$

Here, $Ysn$ is the centroid coordinate of the datum band patterns b1 and b2 in the Y-direction. $\alpha$ is a predetermined coefficient, and is preferably 0.5. $Fysn$ is the ferret diameter of the datum band patterns b1 and b2 in the Y-direction. The ferret diameter is calculated at the step S520 of the subroutine program for the step S500 of the main program. The subscript "n" is substituted by 1 for the datum band pattern b1, and by 2 for the datum band pattern b2.

The form coefficients are the minimum and maximum values of the areas of the datum band patterns b1 and b2, i.e. SsnMIN and SsnMAX, the minimum and maximum values of the products of the ferret diameters thereof, i.e. FsnMIN and FsnMAX, and the minimum and maximum values of the length to width ratio thereof, i.e. HsnMIN and HsnMAX. The form coefficients are calculated by the following formulas:

$SsnMIN = Ssn \times \beta\, min$
$SsnMAX = Ssn \times \beta\, max$
$FsnMIN = Fysn \times Fxsn \times \beta\, min$
$FsnMAX = Fysn \times Fxsn \times \beta\, max$
$HsnMIN = (Fysn/Fxsn) \times \beta\, min$
$HsnMAX = (Fysn/Fxsn) \times \beta\, max$ Here, $Ssn$ is the area of the datum band patterns b1 and b2. $\beta$ min and $\beta$ max are predetermined coefficients, and are preferably 0.6 and 1.5, respectively. As described earlier, $Fysn$ is the ferret diameter of the datum band patterns b1 and b2 in the Y-direction, and $Fxsn$ is the ferret diameter of the band pattern b1 and b2 in the X-direction. The subscript "n" is substituted by 1 for the datum band pattern b1, and by 2 for the datum band pattern b2.

A subroutine program performed in the step, S800, will be hereinafter described with reference to FIG. 7.

First, the accumulator Rx for specifying sample region numbers is set to one (1) at a step, S810. Then, the flags, ICHs, ICHi, KEIJYOs and KEIJYOi, of the sample region 102 corresponding to one (1), i.e. the number set in the accumulator Rx or Rx=1, are read out from the memory unit at a step, S820.

After S820, each of the sample region 102 flags are judged by the flags.

At a step, S830, the sample band pattern b3 is checked whether its position and form agree with those of the normal datum band pattern b2. Namely, the flags of the sample region 102 are checked whether the flag ICHs is zero (0) and the flag KEIJYOs is zero (0), i.e. ICHs=0 and KEIJYOs=0. When the position and form of the sample band pattern b3 are judged to agree with those of the normal datum band pattern b2, the subject is judged to be a normal person at a step, S840.

At a step, S850, the sample band pattern b3 is checked whether its position and form agree with those of the abnormal datum band pattern b1. Namely, the flags of the sample region 102 are checked whether the flag ICHi is zero (0) and the flag KEIJYOi is zero (0), i.e. ICHi=0 and KEIJYOi=0. When the position and form of the sample band pattern b3 are judged to agree with those of the abnormal datum band pattern b1, the subject is judged to be an abnormal person at a step, S860.

At a step, S870, the sample band pattern b3 is checked whether its position agrees with that of the normal datum band pattern b2 and its form is different from that of the normal datum band pattern b2. Namely, the flags of the sample region 102 are checked whether the flag ICHs is zero (0) and the flag KEIJYOs is one (1), i.e. ICHs=0 and KEIJYOs=1. When they are not, the sample band pattern b3 is re-inspected at a step, S890.

At a step, S880, the sample band pattern b3 is checked whether its position agrees with that of the abnormal datum band pattern b1 and its form is different from that of the abnormal datum band pattern b1. Namely, the flags of the sample region 102 are checked whether the flag ICHi is zero (0) and the flag KEIJYOi is one (1), i.e. 1CHi=0 and KEIJYOi=1. When they are not, the sample band pattern b3 is re-inspected at a step, S890. When they are so, the subject is determined to be a carrier at a step, S900.

After performing the steps S840, S890 and S900, the accumulator Rx is increased by 1 at a step, S910. The number set in the accumulator Rx is checked whether it exceeds the number of sample regions 102, 103 and 104 at a step, S920. Here, the number of the sample regions is three (3) in this preferred embodiment. The above-mentioned operation is performed repeatedly until the number set in the accumulator Rx exceeds the number of the sample regions. Namely, the operation is performed repeatedly for all of the sample regions 102, 103 and 104.

In this way, the sample genetic material of the sample region 102 has been determined to be a genetic material of a normal person, the sample genetic material of the sample region 103 has been determined to be a genetic material of an abnormal person, and the sample genetic material of the sample region 104 has been determined to be a genetic material of a carrier person by this subroutine program.

It is apparent from what have been described so far that this preferred embodiment of the electrophoresis pattern analyzer for genetic material according to this invention enables to automate and mechanize the band arrangement pattern analysis and identification operation which has been performed by visually checking with human eyes, thereby enabling mass processing and automated processing of the electrophoresis specimens.

In addition, even when the number of the sample genetic materials arranged in a parallel manner in the electrophoresis specimen has increased, the sample band pattern far away from the datum band pattern can be compared with the datum band pattern precisely. Accordingly, many number of sample genetic materials can be disposed in one (1) electrophoresis specimen.

Further, it is unnecessary to electrically migrate the genetic materials for a long period of time to secure distance between two bands neighboring in the electrophoresis direction, because the positions and forms of the datum band pattern and sample band patterns can be analyzed and identified with the above-mentioned preferred embodiment of the electrophoresis pattern analyzer for genetic material according to this invention more precisely than the conventional visual analysis and identification. Consequently, time required for the analysis and identification has been shortened, and the size of the electrophoresis specimen can be down-sized.

Furthermore, the number of the datum region has been set as one (1) in the above-mentioned preferred embodiment of the electrophoresis pattern analyzer for genetic material according to this invention, however, the preferred embodiment is applicable to the datum region divided into two (2) regions, i.e. one is for a genetic material of a normal person and the other is for a genetic material of an abnormal person. When the number of bands in the datum region and sample regions have been increased the above-mentioned processing method of the preferred embodiment can be employed without changes. As a result, the processing method of the preferred embodiment can be not only applicable to human gene verification for judging parent-children relationships and identifying individuals, but also applicable to verification of all living things.

Moreover, the concentration threshold values have been calculated on the whole electrophoresis specimen in the preferred embodiment of the electrophoresis pattern analyzer for genetic material according to this invention, but they may be calculated on the datum band region and the sample band regions respectively.

Having now fully described the invention, it will be apparent to one of ordinary skill in the art that many changes and modifications can be made thereto without departing from the spirit or scope of the invention as set forth herein.

What is claimed is:

1. An electrophoresis pattern analyzer for genetic material comprising:

an image data generating means for optically reading an electrophoresis specimen having a datum region with a plurality of bands arranged in a direction of electrophoresis and at least one sample region with a plurality of bands arranged in said direction of electrophoresis, said bands being obtained by electrically migrating at least one datum genetic material disposed perpendicularly to said direction of electrophoresis simultaneously with at least one sample genetic material disposed perpendicularly to said direction of electrophoresis, said image data generating means reading said bands two-dimensionally in order to output datum image data including position coordinates and two-dimensional forms of said bands of said datum region and sample image data including position coordinates and two-dimensional forms of said bands of said sample region;

a datum band pattern retrieving means for retrieving datum band patterns concerning said position coordinates of said bands of said datum region in said direction of electrophoresis and said two-dimensional forms of said bands of said datum region from said datum image data, said data band pattern retrieving means retrieving areas, products of ferret diameters and length to width ratios of said bands of said datum region from said two-dimensional forms of said bands of said datum region;

a sample band pattern retrieving means for retrieving sample band patterns concerning said position coordinates of said bands of said sample region in said direction of electrophoresis and said two-dimensional forms of said bands of said sample region from said sample image data, said sample band pattern retrieving means retrieving areas, products of ferret diameters and length to width ratios of said bands of said sample region from said two-dimensional forms of said bands of said sample region; and a band pattern comparing means for comparing said datum band patterns with said sample band patterns and determining characteristics of said sample region, said band pattern comparing means classifying and identifying said bands of said sample region with said bands of said datum region by said retrieved datum and sample area, said products of ferret diameters and said length to width ratios.

2. An electrophoresis band pattern analyzer for genetic material according to claim 1, wherein said datum band pattern retrieving means and said sample band pattern retrieving means retrieve centroid coordinates of said bands of said datum region and said sample region in said direction of electrophoresis as said position coordinates from said two-dimensional forms of said bands of said datum region and said sample region.

3. An electrophoresis band pattern analyzer for genetic material according to claim 2, wherein said datum band pattern retrieving means and said sample band pattern retrieving means retrieve said centroid coordinates in said direction of electrophoresis from centers of said ferret diameters in said direction of electrophoresis, said ferret diameters being calculated from said two-dimensional forms of said bands of said datum region and said sample region.

4. An electrophoresis band pattern analyzer for genetic material according to claim 1, wherein said datum band pattern retrieving means and said sample band pattern retrieving means retrieve a whole concentration-occurrence frequency curve of said bands of said datum region and said sample region from said datum image data and said sample image data, and digitize said whole concentration-occurrence frequency curve to obtain concentration threshold values in order to identify said sample band patterns with said datum band pattern.

5. An electrophoresis pattern analyzer for genetic material comprising:

a CCD two-dimensional photographing apparatus for photographing an electrophoresis specimen having a datum region with a plurality of bands arranged in a direction of electrophoresis and at least one sample region with a plurality of bands arranged in said direction of electrophoresis, said bands being obtained by electrically migrating at least one datum genetic material disposed perpendicularly to said direction of electrophoresis simultaneously with at least one sample genetic material disposed perpendicularly to said direction of electrophoresis, said CCD two-dimensional photographing apparatus photographing said bands two-dimensionally in order to output image data of said electrophoresis specimen including position coordinates and two-dimensional forms of said bands of said datum region and said sample region;

an image processing apparatus for processing said image data output by said CCD two-dimensional photography apparatus, said image processing apparatus retrieving areas, products of ferret diameters and length to width ratios of said bands of said datum region and said sample region from said two-dimensional forms of said bands of said datum region and said sample region, classifying and identifying said bands of said sample region with said bands of said datum region by said areas, said products of ferret diameters and said length to width ratios;

a light generating apparatus for lighting said electrophoresis specimen at rear thereof; and an I/O interface; and an output display apparatus.

6. An electrophoresis band pattern analyzer for genetic material according to claim 5, wherein said image processing apparatus retrieves centroid coordinates of said bands of said datum region and said sample region in said direction of electrophoresis from said two-dimensional forms of said bands of said datum region and said sample region in order to identify said bands of said sample region with said bands of said datum region.

7. An electrophoresis band pattern analyzer for genetic material according to claim 6, wherein said image processing apparatus retrieves said centroid coordinates in said direction of electrophoresis from centers of said ferret diameters in said direction of electrophoresis, said ferret diameters calculated from said two dimensional forms of said bands of said datum region and said sample region.

8. An electrophoresis band pattern analyzer for genetic material according to claim 5, wherein said image processing apparatus retrieves a whole concentration-occurrence frequency curve of said bands of said datum region and said sample region from said image data of said electrophoresis specimen, and digitizes said whole concentration-occurrence frequency curve to obtain concentration threshold values in order to identify said bands of said sample region with said bands of said datum region.

* * * * *